United States Patent
Roettger et al.

(10) Patent No.: US 7,758,897 B2
(45) Date of Patent: Jul. 20, 2010

(54) METHOD FOR THE PRODUCTION OF METAL COMPLEXES

(75) Inventors: Dirk Roettger, Recklinghausen (DE); Ralf Jackstell, Cuxhaven (DE); Matthias Beller, Nienhagen (DE)

(73) Assignee: Evonik Oxeno GmbH, Marl (DE)

( * ) Notice: Subject to any disclaimer, the term of this patent is extended or adjusted under 35 U.S.C. 154(b) by 577 days.

(21) Appl. No.: 10/538,359

(22) PCT Filed: Oct. 24, 2003

(86) PCT No.: PCT/EP03/11773

§ 371 (c)(1), (2), (4) Date: Jun. 13, 2005

(87) PCT Pub. No.: WO2004/052896

PCT Pub. Date: Jun. 24, 2004

(65) Prior Publication Data

US 2006/0058514 A1 Mar. 16, 2006

(30) Foreign Application Priority Data

Dec. 12, 2002 (DE) .............................. 102 57 938

(51) Int. Cl.
- A61K 33/24 (2006.01)
- A61K 33/26 (2006.01)
- C07D 249/08 (2006.01)
- C07D 233/02 (2006.01)

(52) U.S. Cl. .................. 424/617; 424/646; 424/649; 548/262.2; 548/300.1

(58) Field of Classification Search ................ 424/617, 424/646, 649; 548/262.2, 300.1
See application file for complete search history.

(56) References Cited

U.S. PATENT DOCUMENTS

| 7,235,698 | B2 * | 6/2007 | Behenna et al. ............. 568/314 |
| 7,462,745 | B2 | 12/2008 | Nierlich et al. |
| 2004/0059170 | A1 | 3/2004 | Rottger et al. |
| 2004/0242947 | A1 | 12/2004 | Beller et al. |
| 2005/0038273 | A1 | 2/2005 | Rottger et al. |
| 2005/0065387 | A1 | 3/2005 | Beller et al. |
| 2007/0213574 | A1 | 9/2007 | Borgmann et al. |
| 2009/0054710 | A1 | 2/2009 | Borgmann et al. |

FOREIGN PATENT DOCUMENTS

DE 100 62 577 7/2002

OTHER PUBLICATIONS

McGuinness, et al (J.A.C.S., vol. 123, No. 34, 2001).*
McGuinness, et al., (JACS, vol. 123(34), 2001, 8317-8328, esp p. 8318.*
U.S. Appl. No. 10/562,454, filed Dec. 27, 2005, Krissmann, et al.
Jackstell et al. "Efficient telomerization of 1,3-butadiene with alcohols in the presence of in situ generated palladium(0)carbene complexes", Journal of Molecular Catalysis A: Chemical, vol. 185, pp. 105-112, XP002268559 2002.
Jackstell et al. "A Highly Efficient Catalyst for the Telomerization of 1,3-Dienes with Alcohols: First Synthesis of a Monocarbenepalladium(0)- Olefin Complex", Angew. Chem. Int. Ed., vol. 41, No. 6, pp. 986-989, XP002268560 2002.
U.S. Appl. No. 12/307,331, filed Jan. 2, 2009, Brehme et al.

* cited by examiner

*Primary Examiner*—Susannah Chung
(74) *Attorney, Agent, or Firm*—Oblon, Spivak, McClelland, Maier & Neustadt, L.L.P.

(57) ABSTRACT

The invention relates to a process for preparing metal complexes containing carbene ligands by reacting metal compounds with ligand precursors II and/or III and to the use of the thus obtained metal complexes as catalysts.

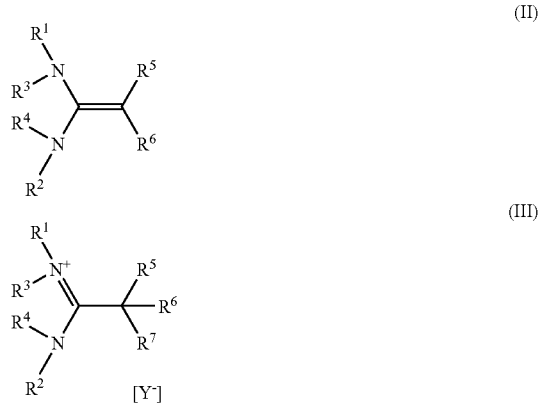

9 Claims, No Drawings

METHOD FOR THE PRODUCTION OF METAL COMPLEXES

The invention relates to a process for preparing metal complexes containing carbene ligands by reacting metal compounds with ligand precursors II and/or III and to the use of the thus obtained metal complexes as catalysts.

Metal complexes which contain, as the central atom, a metal of groups 6 to 10 of the Periodic Table of the Elements and ligands bonded to this metal atom are increasingly being used as catalysts for chemical reactions. Their significance lies in particular in reactions which lead to the formation of carbon-carbon, carbon-hydrogen, carbon-oxygen and carbon-nitrogen bonds. Often, metal complex catalysts are used in industrial processes. Examples of such processes are the hydroformylation of olefins, the hydrogenation of olefins, aldehydes or ketones, for example, metathesis reaction and telomerization.

The ligands which coordinate to the metal atom have an immense influence on the catalytic behavior of the metal complex. Firstly, they exert a stabilizing effect, which is why they are often even used in excess in catalytic reactions. Secondly, activity and selectivity of the catalyst are controllable within a wide range via the type of ligands.

The ligands used are mainly nitrogen compounds, for example amines, or phosphorus(III) compounds, for example phosphines or phosphites. For the telomerization of 1,3-butadiene with methanol, in which mainly 2,7-octadienyl methyl ether is formed, in EP 0 461 222, for example, triphenylphosphine is described as the ligand and palladium as the metal of groups 6-10.

In recent times, N-heterocyclic carbenes are additionally increasingly finding use as ligands in metal complexes. The use of these ligands allows sometimes considerable advantages to be achieved over catalysts which contain only phosphorus ligands. Various possible uses and examples of the use of the N-heterocyclic carbenes as ligands can be found in reviews which document the current state of the art (W. A. Herrmann, Angewandte Chemie 2002, 114, 1342-1363; W. A. Herrmann, T. Weskamp, V. P. W. Böhm, Advances in Organometallic Chemistry, 2001, Vol. 48, page 1-69; L. Jafarpour, S. P. Nolan, *Adv. Organomet. Chem.* 2001, 46, 181; D. Bourissou, O. Guerret, F. P. Gabbai, G. Bertrand, Chem. Rev. 100, 39).

The use of an N-heterocyclic carbene as a ligand in a palladium complex which is used as a catalyst for the telomerization of 1,3-butadiene with methanol is likewise described (R. Jackstell, M. Gómez Andreu, A. Frisch, K. Selvakumar, A. Zapf, H. Klein, A. Spannenberg, D. Röttger, O. Briel, R. Karch, M. Beller, Angewandte Chemie 2002, 114, 128). Here too, distinct improvements over catalyst systems having phosphorus ligands can be demonstrated.

The successes which have been achieved with the N-heterocyclic carbenes as ligands show that individual catalytic problems can be solved with novel metal complexes as catalysts. At the same time, it is necessary that metal complexes which are used as catalysts are obtainable simply and inexpensively.

It is therefore an object of the present invention to provide a process for preparing the metal complexes.

The present invention therefore provides a process for preparing complexes of metals of groups 6 to 10 of the Periodic Table of the Elements by reacting a compound of a metal of groups 6 to 10 of the Periodic Table of the Elements with compounds of the formula II and/or III

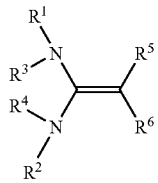

(II)

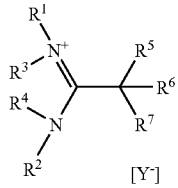

(III)

where $R^1, R^2, R^3, R^4$ are the same or different and are each linear, branched, substituted or unsubstituted, cyclic or alicyclic alkyl groups having from 1 to 24 carbon atoms; substituted or unsubstituted, mono- or polycyclic aryl groups having from 6 to 24 carbon atoms; mono- or polycyclic, substituted or unsubstituted heterocycles having from 2 to 24 carbon atoms; a heteroatom from the group of N, O, S, and $R^3$, $R^4$ may have a covalent bond $R^5, R^6, R^7$ may be the same or different and may each be H, linear, branched, substituted or unsubstituted, cyclic or alicyclic alkyl groups having from 1 to 24 carbon atoms; substituted or unsubstituted, mono- or polycyclic aryl groups having from 6 to 24 carbon atoms, with the proviso that the $R^7$ substituent is not H.

When the ligand precursors used are ionic compounds, they are used as a salt with the counterion [Y⁻].

[Y⁻] is preferably halide, pseudohalide, tetraphenylborate, tetrafluoroborate, tetrachloroborate, hexafluorophosphate, hexafluoroantimonate, tetracarbonylcobaltate, hexafluoroferrate, tetrachloroferrate, tetrachloroaluminate, triflate, bistrifluorosulfonylamide, heptachlorodialuminate, tetrachloropalladate, sulfate, hydrogensulfate, nitrate, nitrite, phosphate, hydrogenphosphate, dihydrogenphosphate, hydroxide, carbonate, hydrogencarbonate, salts of aromatic or aliphatic carboxylic acids, salts of aromatic or aliphatic sulfonic acids or phenoxides.

$R^5, R^6, R^7$ may have the same definitions or, for example, be substituted or unsubstituted aryl-, heteroaryl-, alkyl-, alkenyl-, allyl group, —CN, —COOH, —COO-alkyl-, —COO-Aryl-, —OCO-alkyl-, —OCO-aryl-, —OCOO-alkyl-, —OCOO-aryl-, —CHO, —CO-alkyl-, —CO-aryl-, —O-alkyl-, —O-aryl-, —NH₂, —NH(alkyl)-, —N(alkyl)₂-, —NH(aryl)-, —N(aryl)₂-, —F, —Cl, —Br, —I, —OH, —CF₃, —NO₂, -ferrocenyl, —SO₃H, —PO₃H₂, where the alkyl groups contain from 1 to 24, the alkenyl and heteroaryl groups from 2 to 24 and the aryl groups from 5 to 24, carbon atoms. In the process according to the invention, preference is given to using ligand precursors which satisfy one of the general formulae (V) to (X):

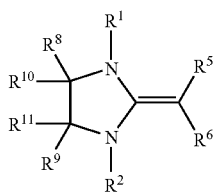

V

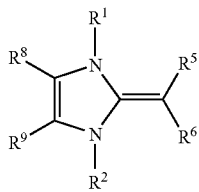

VI

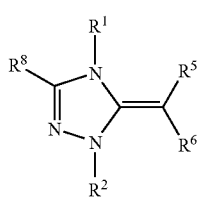

VII

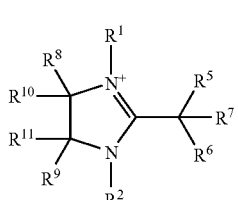

VIII

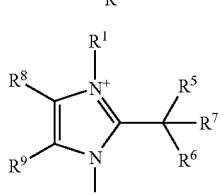

IX

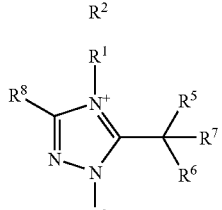

X where $R^1$, $R^2$, $R^5$, $R^6$ and $R^7$ are each as defined above and $R^8$, $R^9$, $R^{10}$ and $R^{11}$ may be the same or different and each be hydrogen or have one of the definitions of $R^1$.

$R^8$, $R^9$, $R^{10}$, $R^{11}$ are preferably the same or different and are each hydrogen, substituted or unsubstituted aryl-, heteroaryl-, alkyl-, alkenyl-, allyl group, —CN, —COOH, —COO-alkyl-, —COO-aryl-, —OCO-alkyl-, —OCO-aryl-, —OCOO-alkyl-, —OCOO-aryl-, —CHO, —CO-alkyl-, —CO-aryl-, —O-alkyl-, —O-aryl-, —NH₂, —NH(alkyl)-, —N(aryl)₂-, —NH(aryl)-, —N(alkyl)₂-, —F, —Cl, —Br, —I, —OH, —CF₃, —NO₂, -ferrocenyl, —SO₃H, —PO₃H₂, where the alkyl groups contain from 1 to 24, the alkenyl and heteroaryl groups from 2 to 24 and the aryl groups from 5 to 24, carbon atoms, and where the $R^8$ and $R^9$ radicals may also be covalently joined.

The $R^1$, $R^2$, $R^3$, $R^4$, $R^5$, $R^6$, $R^7$, $R^8$, $R^9$, $R^{10}$, $R^{11}$ radicals may be the same or different and each have a substituent from the group of —H, —CN, —COOH, —COO-alkyl, —COO-aryl, —OCO-alkyl, —OCO-aryl, —OCOO-alkyl, —OCOO-aryl, —CHO, —CO-alkyl, —CO-aryl, -aryl, -heteroaryl, -alkyl, -alkenyl, -allyl, —O-alkyl, —O-aryl, —NH₂, —NH(alkyl), —N(alkyl)₂, —NH(aryl), —N(alkyl)₂, —F, —Cl, —Br, —I, —OH, —CF₃, —NO₂, -ferrocenyl, —SO₃H, —PO₃H₂, where the alkyl groups contain from 1 to 24, the alkenyl and heteroaryl groups from 2 to 24 and the aryl groups from 5 to 24, carbon atoms.

Substituents having acidic hydrogen atoms may also have metal or ammonium ions instead of the protons.

$R^1$ and $R^2$ may each be the same or different and are in particular isopropyl, tert-butyl, adamantyl, cyclohexyl, benzyl, phenyl, substituted phenyl radicals (for example mesityl, tolyl, xylyl, 2,6-diisopropylphenyl, p-methoxyphenyl, 2,3-dimethoxyphenyl, p-chlorophenyl and mono- or polycyclic rings which contain at least one heteroatom).

These are, for example, radicals which derive from five- and six-membered heteroalkanes, heteroalkenes and heteroaromatics such as 1,4-dioxane, morpholine, γ-pyran, pyridine, pyrimidine, pyrazine, pyrrole, furan, thiophene, pyrazole, imidazole, thiazole and oxazole.

$R^8$, $R^9$, $R^{10}$ and $R^{11}$ may each be the same or different and are in particular hydrogen, methyl, ethyl, phenyl.

In the general formulae (VI) and (IX), the $R^8$ and $R^9$ radicals are additionally together a bridging group in which the substituents are joined together via a covalent bond, and are in particular groups such as —CH=CH—CH=CH— which lead to the formation of a fused aromatic which may optionally be mono- or polysubstituted by the substituents mentioned.

$R^5$, $R^6$, $R^7$ may each be the same or different and are in particular hydrogen, aryl, heteroaryl or alkenyl substituents. Preferably, one of the $R^5$ or $R^6$ radicals is hydrogen, the other an aryl, heteroaryl or alkenyl substituent. Preferred aryl substituents are substituted or unsubstituted phenyl groups; preferred heteroaryl substituents are substituted or unsubstituted pyridyl groups.

The $R^5$ and $R^6$ radicals are additionally together a bridging group in which the substituents are joined together via a covalent bond. This preferably forms a five-, six-, seven-membered ring.

The $R^1$ and $R^5$ radicals may additionally together be a bridging group in which the substituents are joined together via a covalent bond. Together with the N—C=C unit of the compounds III to VIII, this preferably forms a five-, six-, seven-, eight-, nine- or ten-membered ring. When, for example, the $R^1$ and $R^7$ radicals together are the —CH₂—CH₂—CH₂— group, a six-membered cycle is formed.

In the process according to the invention, no compounds of the forms II and/or III are used in which the $R^3$ and $R^4$ radicals, and the $R^5$ and $R^6$ radicals, simultaneously contain two nitrogen atoms and are bridged.

Thus, all tetraaminoethylene derivatives of the general formula

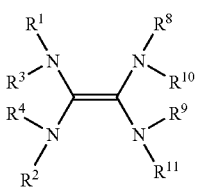

do not form part of the subject matter of the process according to the invention.

The table which follows reproduces examples of ligand precursors used in accordance with the invention.

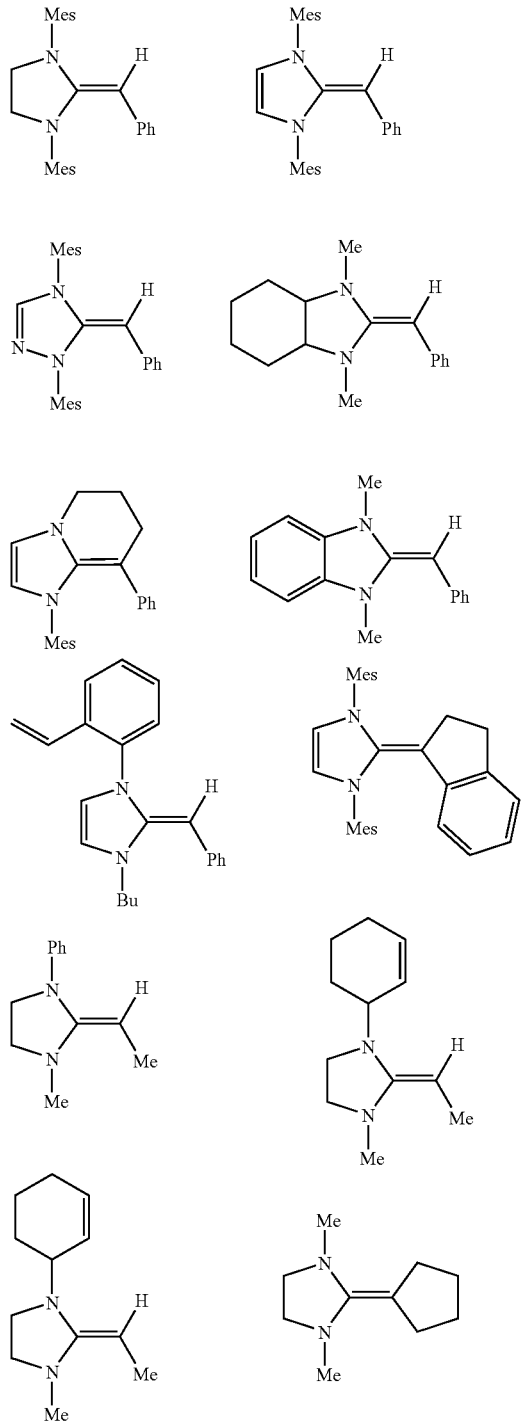

The ligand precursors according to the general formulae (II) to (X) may be prepared synthetically in a simple manner by various routes. The compounds (V) to (VII) may, for example, as known from the literature, be obtained by deprotonating the salts (VIII) to (X) in which $R^7$ is hydrogen (Liebigs Ann. Chem. 1993, 1149-1151; Chem. Ber. 1987, 120, 2053).

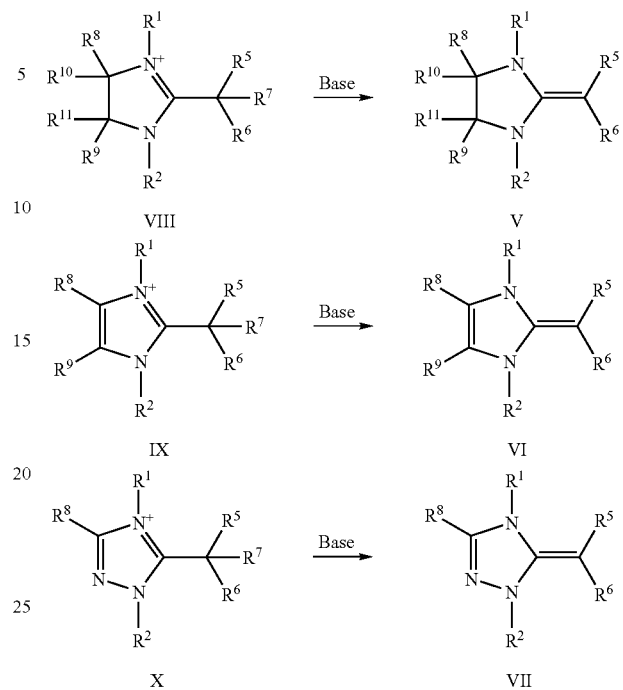

For the compounds (VIII) to (X), various synthetic routes likewise see open; four are illustrated here by way of example.

Synthetic Route 1)

From imidazolium salts, compounds according to the general formula IX may be obtained by deprotonation and subsequent reaction with alkyl halides (cf. Tetrahedron 1988, 44, 7413).

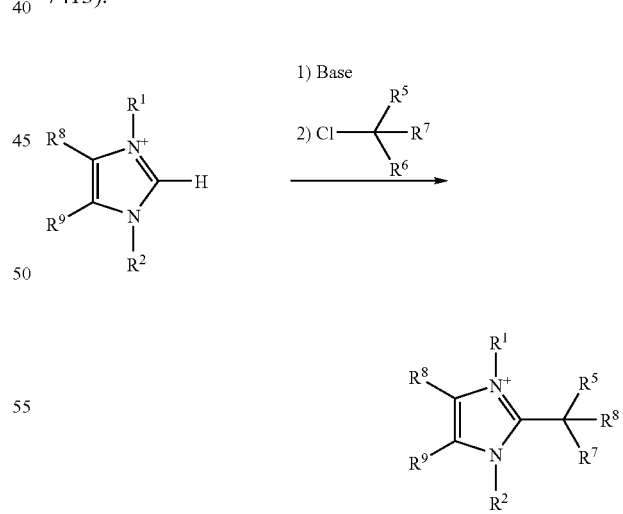

Synthetic Route 2)

Thiolate groups in the 2-position of imidazolium salts may be exchanged by nucleophilic substitution reactions (Liebigs Ann. Chem. 1993, 1149-1151).

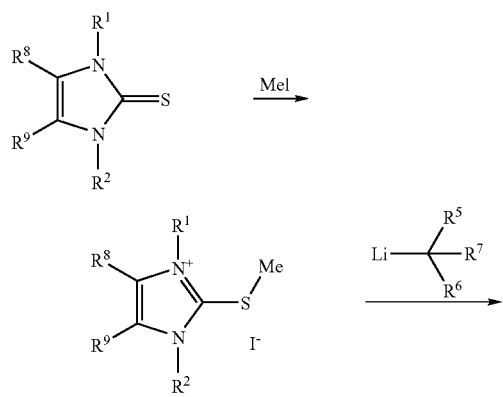

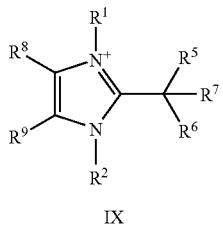

IX

The compounds of the type (VIII) are accessible by reacting 1,2-diamines with orthoesters. As an alternative to the orthoesters, nitriles may optionally be used (J. Med. Chem. 1977, 20, 531).

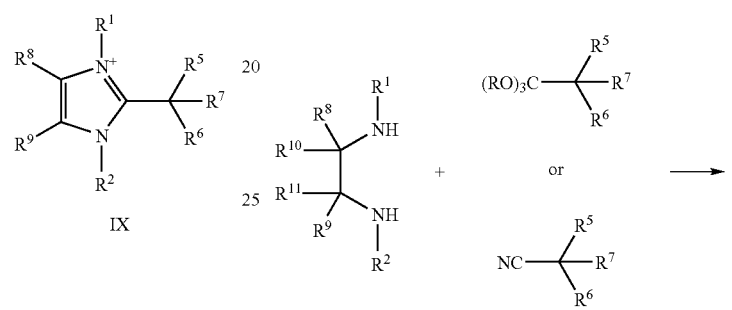

VIII

Synthetic Route 3)

Imidazolium salts of the general formula (IX) are accessible via assembly reactions from α-dicarbonyl compounds, primary amines and aldehyde (WO 91/14678).

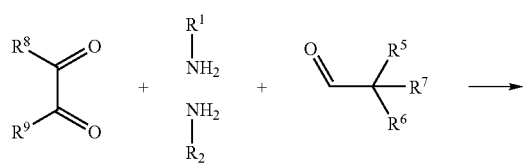

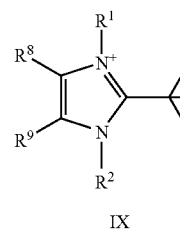

IX

Instead of a one-stage synthesis, a 1,4-diazabutadiene can first be formed from the α-dicarbonyl compound and the amine and then reacted with aldehyde.

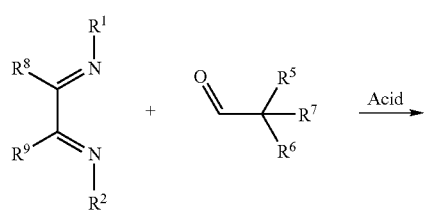

Synthetic Route 4)

Synthesis by quaternization of the nitrogen atom in substituted imidazoles, for example using alkyl halides as the alkylating agent.

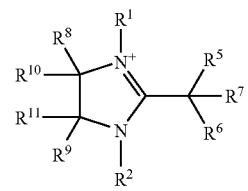

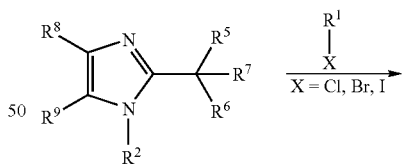

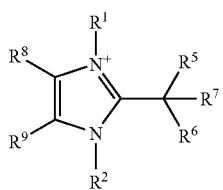

IX

The process according to the invention introduces N-heterocyclic ligands into metal complexes. This can be done with extension of the ligand sphere or with displacement of one or more ligands already present in the metal compound (I) or (XI).

The introduction of the carbene ligand may also be accompanied by the introduction of additional new ligands, by a ligand exchange or by a change in the coordination of ligands already present. This process is not unusual and is also observed in the preparation of metal-carbene complexes via other synthetic routes; cf. EP 0 721 953 B1.

According to literature processes, N-heterocyclic carbene ligands are introduced into metal complexes mainly via three routes: a) by reacting metal compounds with the free N-heterocyclic carbenes, b) by in situ deprotonation of ligand precursors to form the free carbenes, c) by cleaving dimers of carbenes (W. A. Herrmann, T. Weskamp, V. P. W. Böhm, Advances in Organometallic Chemistry, 2001, Vol. 48, page 1-69). The free N-heterocyclic carbenes are often only of limited stability or can only be handled in solution.

The process according to the invention opens up a new route to the metal complexes which uses ligand precursors which are simple to prepare and stable. In the literature, there are to date no experimental descriptions of this reaction. For the addition of imidazolium salts having hydrogen or halogen substituents on metals of group 10, examples are known. For the formation of compounds according to the general formula IX where $R^5=R^6=R^7=H$ from metal carbene complexes too, there are experimental reports (cf. J. Am. Chem. Soc. 2001, 123, 8317). The same reference also cites calculations on the addition of 1,2,3-trimethylimidazolium salts (formula IX where $R1=R2$=methyl, $R^5=R^6=R^7=R^8=R^9=H$) to model complexes of metals of group 10 in the 0 oxidation state, but without being able to confirm them with experimental studies.

WO 02/34722 discloses 1,2,3-substituted imidazolium salts as ionic liquids and the use thereof as solvents, particularly for biphasic reactions. Preference is given to the use as a solvent in particular in reactions in which metal complexes catalyze the reaction. A reaction of the metal compounds with the imidazolium salts is neither described nor mentioned.

As metal compounds of groups 6-10 of the Periodic Table, preference is given to using Ru, Rh, Ni, Pd or Pt. Useful compounds are in particular salts or complexes of the metals. The compounds may contain anionic, cationic or uncharged ligands. Examples of ligands are halides, phosphines, phosphites, phosphonites, phosphinites, amines, nitriles, isonitriles, carbon monoxide, nitrogen monoxide, alkoxides, carboxylates, alkyl substituents, aryl substituents, alkenes, alkynes, aromatics which coordinate via the π-system, such as benzene, cyclopentadienyl, indenyl, carbene ligands (for example Fischer-type, Schrock-type or heterocyclic carbene ligands).

Preference is given to salts or complexes which are obtainable in a simple manner and often commercially available, for example metal halides, metal acetates, metal acetylacetonates, metal carbonyls.

Suitable metal compounds are, for example:

Palladium compounds:
palladium(II) acetate, palladium(II) chloride, palladium (II) bromide, lithium tetrachloro-palladate, palladium(II) acetylacetonate, palladium(0)-dibenzylideneacetone complexes, palladium(II) propionate, bis(acetonitrile)palladium (II) chloride, bis(triphenyl-phosphane)palladium(II) dichloride, bis(benzonitrile)palladium(II) chloride, bis(tri-o-tolylphosphine)palladium(0), allylpalladium chloride (dimer), bis(tricyclohexylphosphine)-palladium(0).

Platinum compounds:
dichloro(1,5-cyclopentadiene)platinum(II), dichlorobis (benzonitrile)platinum(II), dichlorobis(pyridine)platinum (I), dichlorodi(ethylene)platinum(II) dimer, platinum(II) acetylacetonate, platinum(II) chloride, platinum(IV) chloride, tetrakis(triphenylphosphine)platinum(0), chloroplatinic acid, potassium hexachloroplatinate(IV), sodium hexachloroplatinate(IV).

Ruthenium compounds:
dichloro(benzene)ruthenium(II) dimer, dichloro(cymene) ruthenium(II) dimer, dichlorotris(triphenylphosphine)ruthenium(II), dichloro(1,5-cyclooctadiene)ruthenium(II), ruthenium carbonyls, ruthenium chlorides, ruthenium(III) acetylacetonate.

Nickel compounds:
bis(1,5-cyclopentadiene)nickel(0), bis(triphenylphosphine)nickel(II) chloride, bis(triphenylphosphine)nickel dicarbonyl, nickel tetracarbonyl, nickel(II) acetate, nickel(II) acetylacetonate, nickel(II) chloride, nickel(II) 2-ethylhexanoate, nickel(II) sulfate, nickel(II) nitrate.

Rhodium compounds:
rhodium carbonyls such as tetrarhodium dodecacarbonyl, hexarhodium hexadecacarbonyl; rhodium dicarbonyl acetylacetonate, rhodium nitrate, rhodium chloride, $Rh(CO)_2$ (acac) (acac=acetylacetonate), rhodium formate, rhodium acetate, rhodium octanoate, rhodium nonanoate, μ,μ'-dichlororhodium tetracarbonyl, $[Rh(OAc)(COD)]_2$ (Ac=acetyl group, COD=1,5-cyclooctadiene), tris(triphenylphosphine)rhodium chloride.

In the process according to the invention, preference is given to preparing complexes of the general formula (I)

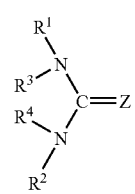

(I)

where [Z] is a metal complex fragment of the general formula $$[L_aM_b][A]_n \qquad (XI)$$

and

M is: metals of groups 6 to 10 of the Periodic Table of the Elements

L is: one or more identical or different mono- or polydentate, charged or uncharged ligands A is: a singly charged anion or the chemical equivalent of a multiply charged anion, b is: an integer of from 1 to 3 a is: an integer of from 0 to 5×b n is: an integer from 0 to 6 and $R^1$, $R^2$, $R^3$, $R^4$ are each defined as specified.

Mono- or polydentate ligands which may be present in addition to the carbene ligand introduced in accordance with the invention in the metal complex fragment L are represented by L in the general formula (XI).

L is hydrogen, the hydrogen ion, halogens, halogen ions, pseudohalides, carboxylate ions, sulfonate ions, amide radicals, alkyl groups, alkylaryl groups, aryl groups, heteroaryl groups, alkenyl groups, alkoxide radicals, nitriles, isonitriles, mono- or diolefins, alkynes, π-aromatic radicals, cyclopentadienyl, indenyl, phosphines, phosphites, phosphinites, phosphonites, phosphorus aromatics, acetylacetonate, carbon monoxide, nitrogen monoxide or carbene ligands, where the alkyl groups contain from 1 to 24, the alkenyl and heteroaryl groups from 2 to 24, and the aryl groups from 5 to 24, carbon atoms, and may each be substituted or unsubstituted. When a plurality of L ligands are present, they may be the same or different.

In the general formula (XI), A is halide, pseudohalide, tetraphenylborate, tetrafluoroborate, tetrachloroborate, hexafluorophosphate, hexafluoroantimonate, tetracarbonylcobaltate, hexafluoroferrate, tetrachloroferrate, tetrachloroaluminate, triflate, bistrifluorosulfonylamide, heptachlorodialuminate, tetrachloropalladate, sulfate, hydrogensulfate, nitrate, nitrite, phosphate, hydrogenphosphate, dihydrogenphosphate, hydroxide, carbonate, hydrogencarbonate, salts of aromatic or aliphatic carboxylic acids, salts of aromatic or aliphatic sulfonic acids and phenoxides.

Preference is given to metal complex fragments according to the general formula (XI) in which b equals one.

For the preparation of the metal complexes (I), a stoichiometric amount of ligand precursor according to the general formulae (III) to (X) is necessary. However, when a superstoichiometric amount of ligand precursor is used, better yields of the compounds (I) are often obtained. Typically, the molar ratio of ligand precursor to metal compound is therefore from 100:1 to 1:1, preferably from 10:1 to 1:1.

The process according to the invention for preparing metal complexes of the formula (I) is preferably carried out in the presence of solvents. Suitable solvents include aliphatic, cycloaliphatic and aromatic hydrocarbons, for example $C_3$-$C_{20}$-alkanes, mixtures of lower alkanes ($C_3$-$C_{20}$), cyclohexane, cyclooctane, ethylcyclohexane, alkenes and polyenes, vinylcyclohexene, 1,3,7-octatriene, the $C_4$ hydrocarbons from $C_4$ cuts from crackers, benzene, toluene and xylene; polar solvents, for example primary, secondary and tertiary alcohols, di- and polyols (ethylene glycol, diethylene glycol, triethylene glycol, tetraethylene glycol, polyethylene glycol, glycerol), primary, secondary and tertiary amines, ammonia, amides, for example acetamide, dimethylacetamide and dimethylformamide, nitriles, for example acetonitrile and benzonitrile, ketones, for example acetone, methyl isobutyl ketone and diethyl ketone; carboxylic esters, for example ethyl acetate, ethers, for example dipropyl ethers, MTBE, diethyl ether, dimethyl ether, methyl octyl ether, 3-methoxyoctane, 1-methoxy-2,7-octadiene, 3-methoxy-1,7-octadiene, dioxane, tetrahydrofuran, anisole, alkyl and aryl ethers of ethylene glycol, diethylene glycol, triethylene glycol, tetraethylene glycol and polyethylene glycol, and other polar solvents, for example sulfolane, dimethyl sulfoxide, ethylene carbonate, propylene carbonate and water. Ionic liquids too, for example imidazolium or pyridinium salts, may be used as solvents.

The solvents are used alone or as mixtures of different solvents.

The metal complexes (I) are preferably used as catalysts. It is a preferred embodiment of the process according to the invention to generate the metal complexes (I) in situ as a catalyst or catalyst precursor. In this case, the solvents utilized are preferably reactants which are present in liquid form under the reaction conditions and are converted in the catalysis. They may, for example, be olefins, halides or alcohols. These may in turn be used in mixtures with the suitable solvents already mentioned.

The temperature at which the metal complexes (I) are prepared is from −135° C. to 200° C., preferably from −78° C. to 160° C. The pressure at which the metal complexes (I) are prepared is from 1 to 125 bar.

The metal complexes (I) can be prepared in accordance with the invention in the presence of compounds which can coordinate to metal centers as ligands. These include solvents capable of coordination, such as tetrahydrofuran or acetonitrile, and compounds which are known as ligands suitable for metals. These include, for example, phosphorus(III) compounds such as phosphines, phosphites, phosphinites, phosphonites, phosphabenzenes, nitriles, isonitriles, alkenes, alkynes, dienes, halides, amines.

For the preparation of the metal complexes (I) in the process according to the invention, oxidizing or reducing agents may be added to the reaction. The addition of oxidizing or reducing agents allows a change, in some cases additional, in the oxidation state of the metal. Examples of oxidizing and reducing agents are hydrazine, hydrogen peroxide, formic acid, hydrogen, oxygen, air, stannanes, silanes, alcohols, ionic hydrides or amines.

The metal complexes (I) are prepared, depending on the particular system, under acidic, neutral or basic conditions. These conditions may be established appropriately by adding acids, bases or buffers. The acids used are, for example, mineral acids (sulfuric acid, hydrochloric acid, phosphoric acid), carboxylic acids (formic acid, acetic acid, benzoic acid), sulfonic acids or phenols. Typical bases are, for example, alkali metal and alkaline earth metal hydroxides, (sodium hydroxide, calcium hydroxide), alkali metal and alkaline earth metal carbonates, (sodium carbonate, cesium carbonate), amines, alkoxides and phenoxides (sodium methoxide, potassium t-butoxide, sodium phenoxide), alkali metal and alkaline earth metal hydrides (sodium hydride), and alkyl- or aryl-metal compounds such as butyllithium, butylmagnesium chloride, phenyllithium.

The metal complexes prepared in accordance with the invention may be isolated in substance and used as a catalyst, or generated in situ and used directly as a catalyst or precatalyst. Precatalyst refers in general and in the context of this invention to a substance, here a metal complex, from which the active catalyst species are formed under catalysis conditions. This may proceed, for example, with loss of one or more of the ligands present (for example L in (XI)) and coordination of the substrate.

Examples of catalytic reactions in which the metal complexes (I) prepared in accordance with the invention may be used are hydroformylation, hydrogenation, aryl amination, hydrosilylation, carbon-carbon coupling reactions, (for example Heck reaction, Suzuki coupling, Kumada coupling, Stille coupling, Miyaura coupling, the Sonogashira coupling), olefin metathesis, olefin dimerization, olefin oligomerization, cyclopropanation, reduction of haloarenes and polymerization (homo- and copolymerization). It is possible to carry out the process according to the invention in such a way that the metal complexes (I) are formed in situ as a catalyst or precatalyst in the abovementioned reactions.

The present invention therefore provides the abovementioned processes which are carried out in the presence of the metal complexes (I), of the metal complexes (I) prepared in accordance with the invention, or of the compounds II to X as ligand precursors.

Preferred catalytic reactions in which the metal complexes (I) prepared in situ or in substance in accordance with the invention are used as a catalyst or precatalyst are catalytic reactions of olefins or dienes to give olefins or dienes having altered carbon number, in particular the metathesis of olefins and the telomerization of noncyclic, conjugated dienes such as butadiene with alcohols, water or amines.

The molar ratio of one or more of the compounds II to X to the metal of group 6-10 of the Periodic Table is 1:100, in particular 1:10.

The temperature at which catalytic reactions with the complexes prepared by the process according to the invention are carried out, here in particular the telomerization of butadiene with methanol, is in the range between −78° C. and 200° C., preferably between 20° C. and 160° C. Preference is given to using from 0.00001 mol % to 5 mol % of metal compound (I) based on the substrate to be converted, particular preference to amounts between 0.0001 mol % to 1 mol %.

Depending on the requirement, acids or bases may be added to the catalytic reaction. In addition, further ligands or ligand precursors may be present in addition to the metal complex (I). Preference is given to using as additional ligands phosphorus(III) compounds such as phosphines, phosphites, phosphinites, phosphonites and compounds according to the general formulae (II) to (X). The molar ratio of excess ligand to the metal complex (I) is from 500:1 to 0:1, preferably from 100:1 to 0:1, more preferably from 50:1 to 0:1, per ligand.

The catalytic reactions using the metal complexes prepared by the process according to the invention may be carried out as continuous or batchwise processes. Processes for carrying out catalytic reactions are described in the literature and adequately known to those skilled in the art.

Optionally, the process according to the invention may be carried out during the reaction to be catalyzed by the complex (I).

It is therefore possible to prepare the metal complexes (I) in situ from the compounds II to X and one of the metals mentioned as catalysts in hydroformylations, hydrogenations, aryl aminations, hydrosilylations, Heck reactions, Suzuki couplings, Kumada couplings, Stille couplings, Miyaura couplings, Sonogashira couplings, olefin metatheses, olefin dimerization, olefin oligomerizations, cyclopropanations, reduction of haloarenes, polymerizations or telomerization reactions, or they may be used as a catalyst in these reactions.

Based on R. Jackstell, M. Gómez Andreu, A. Frisch, K. Selvakumar, A. Zapf, H. Klein, A. Spannenberg, D. Röttger, O. Briel, R. Karch, M. Beller, Angewandte Chemie 2002, 114, 128, in the context of this invention, telomerization refers generally to the reaction of olefins having conjugated double bonds (conjugated dienes) in the presence of a nucleophile (telogen). The main products obtained are compounds which are formed from two equivalents of the diene and one equivalent of the nucleophile. The telomerization of dienes is described comprehensively in the technical literature (WO 91/09822, U.S. Pat. No. 4,642,392, U.S. Pat. No. 4,831,183, DE 2 137 291, U.S. Pat. Nos. 5,030,792, 4,334,117, 4,356,333, 5,057,631, EP 0 296 550, WO 98/08 794, DE 195 23 335).

The products of the telomerization reaction have industrial significance as versatile precursors for solvents, plasticizers, fine chemicals and active ingredient precursors. Octadienol, octadienyl ethers or octadienyl esters, obtainable from 1,3-butadiene, are potential intermediates in processes for preparing corresponding alkenes.

The telomerization of dienes with nucleophiles is a method of industrial interest for upgrading inexpensive, industrially available dienes. Owing to the good availability, the use of butadiene, isoprene or cracker cuts comprising these dienes is of particular interest. To date, the telomerization of 1,3-butadiene is, however, employed practically only by Kuraray in the fine chemicals field for the synthesis of 1-octanol. Reasons which prevent wider use of telomerization processes include inadequate catalyst activities, catalyst productivities and selectivity problems of telomerization catalysts. Thus, the known telomerization processes lead to high catalyst costs and/or by-products which prevent industrial scale realization.

The catalysts used mainly have palladium as the central atom and phosphorus ligands. These catalysts afford, for example, in the telomerization of butadiene with methanol, generally mixtures of the products 1a, 1b, 2, 3 shown. Main products are the desired industrially important linear telomers 1a and 1b. However, significant proportions of the branched telomer 2 and of 1,3,7-octatriene 3 are formed.

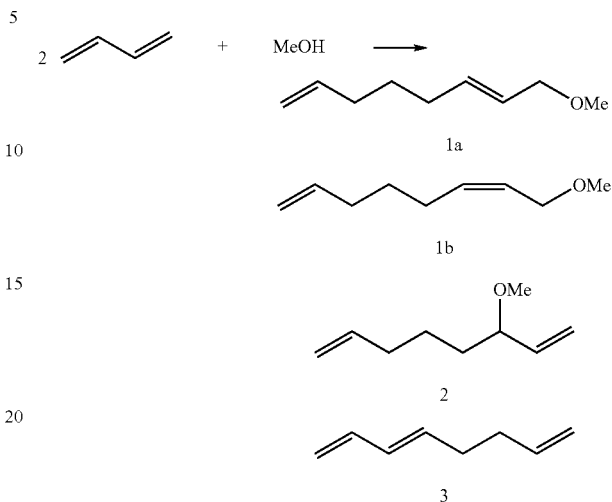

In addition, 4-vinyl-1-cyclohexene (Diels-Alder product of butadiene) is formed in variable yields, and also, generally in only small amounts, further by-products. This spectrum of products is found generally also when other nucleophiles having active hydrogen atoms are used, in which case the corresponding radicals of the particular nucleophile occur in place of the methoxy group.

The significant formation of the by-products mentioned is a further reason which makes an implementation of an economically viable and environmentally friendly process extremely difficult. Even though the telomerization of butadiene with methanol has already been intensively researched and patented by several companies, it has not been possible to satisfactorily solve the abovementioned problems.

The use of the complexes prepared in accordance with the invention as catalysts or catalyst precursors in the telomerization of noncyclic olefins having at least two conjugated double bonds (XII) with a nucleophile (XIII) can achieve distinct improvements in the selectivities.

In the telomerization in the process according to the invention, it is possible in principle to use all noncyclic olefins having at least two conjugated double bonds. In the context of this invention, preference is given to using 1,3-butadiene and isoprene (2-methyl-1,3-butadiene). It is possible to use either the pure dienes or mixtures which comprise these dienes.

The 1,3-butadiene/isoprene-containing mixtures used are preferably mixtures of 1,3-butadiene or isoprene with other $C_4$ hydrocarbons and/or $C_5$ hydrocarbons. Such mixtures are obtained, for example, in cracking processes for the production of ethene, in which refinery gases, naphtha, gas oil, LPG (liquefied petroleum gas), NGL (natural gas liquid), etc. are converted. The $C_4$ cuts obtained as a by-product in these processes contain different amounts of 1,3-butadiene depending on the cracking process. Typical 1,3-butadiene concentrations in the $C_4$ cut, as obtained from a naphtha steam cracker, are 20-70% 1,3-butadiene.

The $C_4$ components n-butane, i-butane, 1-butene, cis-2-butene, trans-2-butene and i-butene, which are likewise present in these cuts, only insignificantly disrupt the reaction in the telomerization step, if at all.

In contrast, alkynes, especially vinylacetylene, can act as moderators in the telomerization reaction. It is therefore advantageous to remove the C4 alkynes and optionally also cumulenes such as 1,2-butadiene beforehand (for example according to DE 195 23 335). This may, if possible, be effected by physical processes such as distillation or extraction. By a chemical route, the alkynes may be reduced to alkenes or alkanes by selective hydrogenations, and the accumulated dienes reduced to monoenes. Processes for such hydrations are prior art and are described, for example, in WO 98/12160, EP-A-0 273 900, DE-A-37 44 086 or U.S. Pat. No. 4,704,492.

The nucleophiles (XIII) used are preferably water, alcohols and phenols, for example methanol, ethanol, n-propanol, isopropanol, allyl alcohol, butanol, octanol, 2-ethylhexanol, isononanol, benzyl alcohol, cyclohexanol, cyclopentanol, 2-methoxyethanol, phenol or 2,7-octadien-1-ol dialcohols, for example ethylene glycol, 1,2-propanediol, 1,3-propanediol, 1,4-butanediol, 1,2-butanediol, 2,3-butanediol and 1,3-butanediol polyols, for example glycerol, glucose, sucrose, hydroxy compounds, for example α-hydroxyacetic esters carboxylic acids, for example acetic acid, propanoic acid, butanoic acid, isobutanoic acid, benzoic acid, 1,2-benzenedicarboxylic acid, 1,3-benzenedicarboxylic acid, 1,4-benzenedicarboxylic acid, 1,2,4-benzenetricarboxylic acid, ammonia, primary amines, for example methylamine, ethylamine, propylamine, butylamine, octylamine, 2,7-octadienylamine, dodecylamine, aniline, ethylenediamine or hexamethylenediamine, secondary amines such as dimethylamine, diethylamine, N-methylaniline, bis(2,7-octadienyl)amine, dicyclohexylamine, methylcyclohexylamine, pyrrolidine, piperidine, morpholine, piperazine or hexamethyleneimine.

Telogens which can themselves be obtained by a telomerization reaction may be used directly or else formed in situ. For example, 2,7-octadien-1-ol can be formed in situ from water and butadiene in the presence of the telomerization catalyst, 2,7-octadienylamine from ammonia and 1,3-butadiene, etc.

Nucleophiles (XIII) used with particular preference are water, methanol, ethanol, n-butanol, allyl alcohol, 2-methoxyethanol, phenol, ethylene glycol, 1,3-propanediol, glycerol, glucose, sucrose, acetic acid, butanoic acid, 1,2-benzenedicarboxylic acid, ammonia, dimethylamine and diethylamine.

The telomerization is preferably carried out in the presence of a solvent.

The solvent used is generally the nucleophile used when it is present as a liquid under reaction conditions. However, it is also possible to use other solvents. The solvents used should be substantially inert. Preference is given to adding solvents when nucleophiles are used which are present as solids under reaction conditions, or in the case of products which would be obtained as solids under the reaction conditions. Suitable solvents include aliphatic, cycloaliphatic and aromatic hydrocarbons, for example $C_3$-$C_{20}$-alkanes, mixtures of lower alkanes ($C_3$-$C_{20}$), cyclohexane, cyclooctane, ethylcyclohexane, alkenes and polyenes, vinylcyclohexene, 1,3,7-octatriene, the $C_4$ hydrocarbons from $C_4$ cuts from crackers, benzene, toluene and xylene; polar solvents, for example tertiary and secondary alcohols, amides, for example acetamide, dimethylacetamide and dimethylformamide, nitriles, for example acetonitrile and benzonitrile, ketones, for example acetone, methyl isobutyl ketone and diethyl ketone; carboxylic esters, for example ethyl acetate, ethers, for example dipropyl ether, MTBE, diethyl ether, dimethyl ether, methyl octyl ether, 3-methoxyoctane, dioxane, tetrahydrofuran, anisole, alkyl and aryl ethers of ethylene glycol, diethylene glycol and polyethylene glycol, and other polar solvents, for example sulfolane, dimethyl sulfoxide, ethylene carbonate, propylene carbonate and water. Ionic liquids too, for example imidazolium or pyridinium salts, may be used as solvents. The solvents may be used alone or as mixtures of different solvents or nucleophiles.

The temperature at which the telomerization reaction is performed is preferably between 10 and 180° C., in particular between 30 and 120° C., more preferably between 40 and 100° C. The reaction pressure is from 1 to 125 bar, preferably from 1 to 64 bar, more preferably from 1 to 26 bar.

Metal compounds (II) used with preference in the telomerization are salts or complexes of palladium, for example palladium(II) acetate, palladium(II) chloride, palladium(II) bromide, lithium tetrachloropalladate, palladium(II) acetylacetonate, palladium(0)-dibenzylideneacetone complexes, palladium(II) propionate, bis(acetonitrile)palladium(II) chloride, bis(triphenylphosphine)palladium(II) dichloride, bis(benzonitrile)palladium(II) chloride, bis(tri-o-tolylphosphine)palladium(0).

The concentration of the catalyst in the telomerization reaction, reported formally in ppm (by mass) of catalyst metal based on the total mass, is from 0.01 ppm to 1000 ppm, preferably from 0.5 to 100 ppm, more preferably from 1 to 50 ppm.

When the catalyst for the telomerization is prepared in situ from a metal compound and a ligand precursor of the general formulae (II) to (X), the ligand precursor is preferably used in a ratio [mol/mol] of ligand precursor to metal of from 100:1 to 1:1, more preferably from 10:1 to 1:1.

Additional ligand precursor may be introduced into the process at any time in the reaction. Further ligands, for example phosphorus ligands such as triphenylphosphine, may likewise be present in the reaction mixture.

Owing to the catalyst activities and stabilities, it is possible in the telomerization to use extremely small amounts of catalyst. In addition to a process in which the catalyst is reused, the option is thus also opened up of not recycling the catalyst. Both variants have already been described in the patent literature (WO 90/13531, U.S. Pat. Nos. 5,254,782, 4,642,392).

It is often advantageous to carry out the telomerization reaction in the presence of bases. Preference is given to using basic components having a $pK_b$ of less than 7, especially compounds selected from the group of amines, alkali metal salts, alkaline earth metal salts, alkoxides and phenoxides.

Suitable basic components are, for example, amines such as trialkylamines which may be alicyclic or/and open-chain, amides, alkali metal or/and alkaline earth metal salts of aliphatic or/and aromatic carboxylic acids such as acetates, propionates, benzoates or corresponding carbonates, hydrogencarbonates, alkoxides of alkali and/or alkaline earth elements, phosphates, hydrogenphosphates or/and hydroxides, preferably of lithium, sodium, potassium, calcium, magnesium, cesium, ammonium and phosphonium compounds. Preferred additives are hydroxides, alkoxides and phenoxides of the alkali and alkaline earth elements.

In general, the basic component is used in the telomerization reaction between 0.01 mol % and 10 mol % (based on the olefin), preferably between 0.1 mol % and 5 mol % and most preferably between 0.2 mol % and 1 mol %. The ratio [mol/mol] between diene and nucleophile used is from 1:1000 to 100:1, preferably from 1:50 to 10:1, more preferably from 1:10 to 2:1.

The process for telomerization using the complexes prepared in accordance with the invention as catalysts or catalyst precursors may be operated continuously or batchwise, and is not restricted to the use of certain reactor types. Examples of reactors in which the reaction can be carried out are stirred tank reactors, stirred tank batteries, flow tubes and loop reactors. Combinations of different reactors are also possible, for example a stirred tank reactor with downstream flow tube.

The catalysts employed for metathesis reactions are often complexes of osmium and in particular of ruthenium. It has been possible in recent times to obtain novel catalysts having improved properties from complexes which have phosphine ligands and are known in principle by introducing heterocyclic carbene ligands. In addition to the use of metal complexes of defined structure, methods for the in situ preparation of metathesis-active catalysts have also been described (WO 0058322, DE 19815275, EP 1022282, WO 0071554, WO 0220535).

In the process according to the invention, metathesis-active metal complexes are obtained by reacting metal compounds with ligand precursors according to the general formulae (II) to (X).

The catalysts are suitable for ROMP (ring-opening metathesis polymerization), RCM (ring-closing metathesis) and ADMET (acyclic diene metathesis). The metal compounds used are preferably compounds of ruthenium.

What is claimed is:

1. A process for making a metal complex, the process comprising:

reacting a compound of a metal of groups 6 to 10 of the Periodic Table of the Elements with at least one compound selected from the group of compounds having formulae II and III

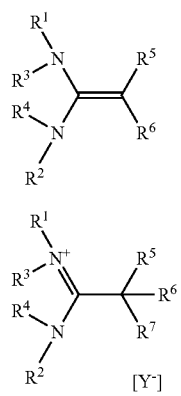

wherein $R^1$, $R^2$, $R^3$ and $R^4$ are the same or different and each is a linear, branched, substituted or unsubstituted, cyclic or alicyclic alkyl group having from 1 to 24 carbon atoms; a substituted or unsubstituted, mono- or polycyclic aryl group having from 6 to 24 carbon atoms; or a mono- or polycyclic, substituted or unsubstituted heterocycle having from 2 to 24 carbon atoms and having a heteroatom selected from the group consisting of N, O and S, and $R^3$ and $R^4$ are linked by a covalent bond;

wherein $R^5$, $R^6$ and $R^7$ are optionally the same or different and each is H; a linear, branched, substituted or unsubstituted, cyclic or alicyclic alkyl group having from 1 to 24 carbon atoms; or a substituted or unsubstituted, mono- or polycyclic aryl group having from 6 to 24 carbon atoms, with the proviso that when groups $R^3$ and $R^4$ in formula are bonded together to form an imidazole ring, the metal of the metal compound reactant can not be a member of group 10;

wherein the at least one compound selected from the group of compounds having formulae II and III is selected from the group of compounds having formulae V, VI, VII, VIII, IX and X

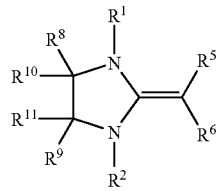

V

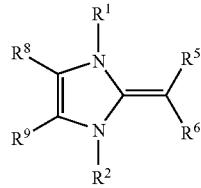

VI

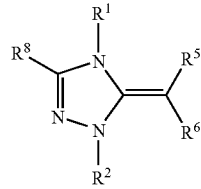

VII

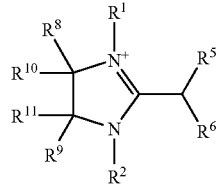

VIII

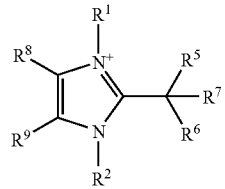

IX

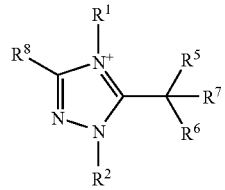

X wherein $R^8$, $R^9$, $R^{10}$ and $R^{11}$ are the same or different and are each H or have one of the definitions of $R^1$; and wherein the metal complex made by the process is represented by a formula (I)

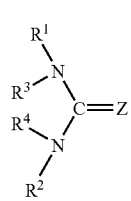

(I)

in which
Z is a metal complex fragment of the formula:

$$[L_aM_b][A]_n \quad \text{(XI) and}$$

M is a metal of groups 6 to 10 of the Periodic Table of the Elements,

L is one or more identical or different mono- or polydentate, charged or uncharged ligands, A is a singly charged anion or the chemical equivalent of a multiply charged anion, b is an integer from 1 to 3, a is an integer from 0 to 5×b, and n is an integer from 0 to 6.

2. The process as claimed in claim 1, wherein L in formula (XI) is hydrogen, the hydrogen ion, halogens, halogen ions, pseudohalides, carboxylate ions, sulfonate ions, amide radicals, alkyl groups, alkylaryl groups, aryl groups, heteroaryl groups, alkenyl groups, alkoxide radicals, nitriles, isonitriles, mono- or diolefins, alkynes, π-aromatic radicals, cyclopentadienyl, indenyl, phosphines, phosphates, phosphinites, phosphonites, phosphorus aromatics, acetylacetonate, carbon monoxide, nitrogen monoxide or carbene ligands, where the alkyl groups contain from 1 to 24 carbon atoms, the alkenyl and heteroaryl groups from 2 to 24 carbon atoms, and the aryl and alkylaryl groups from 5 to 24 carbon atoms, and optionally are each substituted or unsubstituted.

3. The process as claimed in claim 1, wherein A in formula (XI) is halide, pseudohalide, tetraphenylborate, tetratfluoroborate, tetrachloroborate, hexafluorophosphate, hexafluoroantimonate, tetracarbonylcobaltate, hexafluoroferrate, tetrachloroferrate, tetrachloroaluminate, triflate, bistrifluorosulfonylamide, heptachlorodialuminate, tetrachloropalladate, sulfate, hydrogensulfate, nitrate, nitrite, phosphate, hydrogenphosphate, dihydrogenphosphate, hydroxide, carbonate, hydrogencarbonate, salt of aromatic or aliphatic carboxylic acid, salt of aromatic or aliphatic sulfonic acid, or phenoxide.

4. The process as claimed in claim 1, wherein the metal of groups 6 to 10 of the Periodic Table is Ru, Rh, Ni, Pd, or Pt.

5. The process as claimed in claim 1, wherein a molar ratio of the compound of a metal of groups 6 to 10 of the Periodic Table of the Elements to the at least one compound selected from the group of compounds having formulae II and III is in a range of from 1 to 100.

6. A method of telomerization, comprising:
reacting an olefin with a nucleophile in the presence of a catalyst which is the metal complex made by the process of claim 1.

7. The method of claim 6, wherein said olefin is a conjugated diolefin and the nucleophile is an aliphatic alcohol.

8. A method, comprising:
conducting a hydroformylation, a hydrogenation, an aryl amination, a hydrosilylation, a Heck reaction, a Suzuki coupling, a Kumada coupling, a Stille coupling, a Miyaura coupling, a Sonogashira coupling, an olefin metathesis, a cyclopropanation, a reduction of a haloarene or a polymerization reaction in the presence of a catalyst of the metal complex made by the process of claim 1.

9. A process, comprising:
reacting a compound of a metal of groups 6 to 10 of the Periodic Table of the Elements with at least one compound selected from the group consisting of compounds having the formulae V, VII, VIII and X

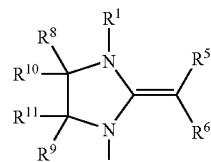

V

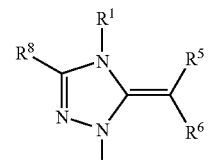

VII

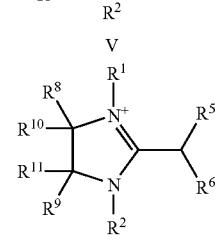

VIII

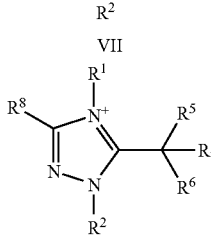

X wherein $R^1$ and $R^2$ are the same or different and each is a linear, branched, substituted or unsubstituted, cyclic or alicyclic alkyl group having from 1 to 24 carbon atoms; a substituted or unsubstituted, mono- or polycyclic aryl group having from 6 to 24 carbon atoms; or a mono- or polycyclic, substituted or unsubstituted heterocycle having from 2 to 24 carbon atoms and having a heteroatom selected from the group consisting of N, O and S wherein $R^5$, $R^6$ and $R^7$ are optionally the same or different and each is H; a linear, branched, substituted or unsubstituted, cyclic or alicyclic alkyl group having from 1 to 24 carbon atoms; or a substituted or unsubstituted, mono- or polycyclic aryl group having from 6 to 24 carbon atoms; and wherein $R^8$, $R^9$, $R^{10}$ and $R^{11}$ are the same or different and are each H or have one of the definitions of $R^1$.

* * * * *